US00PP21952P2

(12) United States Plant Patent
Larsen

(10) Patent No.: US PP21,952 P2
(45) Date of Patent: May 31, 2011

(54) ***OSTEOSPERMUM* PLANT NAMED 'SUNBRE0901'**

(50) Latin Name: *Osteospermum ecklonis*
Varietal Denomination: SUNBRE0901

(75) Inventor: Bjarne Nyholm Larsen, Odense N. (DK)

(73) Assignee: Sunny Gronnegyden APS, Odense (DK)

( * ) Notice: Subject to any disclaimer, the term of this patent is extended or adjusted under 35 U.S.C. 154(b) by 0 days.

(21) Appl. No.: 12/658,728

(22) Filed: Feb. 12, 2010

(51) Int. Cl.
*A01H 5/00* (2006.01)

(52) U.S. Cl. ..... Plt./360

(58) Field of Classification Search ..... Plt./360
See application file for complete search history.

*Primary Examiner* — Kent L Bell
(74) *Attorney, Agent, or Firm* — C. A. Whealy

(57) ABSTRACT

A new and distinct cultivar of *Osteospermum* plant named 'Sunbre0901', characterized by its mounding and outwardly spreading plant habit; freely branching growth habit; freely flowering habit; daisy-type inflorescences with greyed yellow-colored ray florets; and good garden performance.

2 Drawing Sheets

Botanical designation: *Osteospermum ecklonis.*
Cultivar denomination: 'SUNBRE0901'.

BACKGROUND OF THE INVENTION

The present invention relates to a new and distinct cultivar of *Osteospermum* plant, botanically known as *Osteospermum ecklonis*, and hereinafter referred to by the name 'Sunbre0901'.

The new *Osteospermum* plant is a product of a planned breeding program conducted by the Inventor in Odense, Denmark. The objective of the program is to create and develop new *Osteospermum* plants with uniformly mounded plant habit, freely flowering habit and attractive inflorescence coloration.

The new *Osteospermum* plant originated from a cross-pollination by the Inventor in June, 2005 of a proprietary selection of *Osteospermum ecklonis* identified as code number 90.008.03, not patented, as the female, or seed parent with the *Osteospermum ecklonis* 'Sunny Florence', disclosed in U.S. Plant Pat. No. 17,307, as the male, or pollen, parent. The new *Osteospermum* was discovered and selected by the Inventor as a single flowering plant within the progeny of the stated cross-pollination in a controlled greenhouse environment in Odense, Denmark in June, 2006.

Asexual reproduction of the new *Osteospermum* plant by terminal cuttings in a controlled greenhouse environment in Odense, Denmark since November, 2006, has shown that the unique features of this new *Osteospermum* plant are stable and reproduced true to type in successive generations.

SUMMARY OF THE INVENTION

Plants of the new *Osteospermum* have not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'Sunbre0901'.

These characteristics in combination distinguish 'Sunbre0901' as a new and distinct cultivar of *Osteospermum:*

1. Mounding and outwardly spreading plant habit.
2. Freely branching growth habit.
3. Freely flowering habit.
4. Daisy-type inflorescences with greyed yellow-colored ray florets.
5. Good garden performance.

Plants of the new *Osteospermum* differ from plants of the female parent selection in the following characteristics:

1. Plants of the new *Osteospermum* are more outwardly spreading than and not as upright as plants of the female parent selection.
2. Plants of the new *Osteospermum* and the female parent selection differ in ray floret color as plants of the female parent selection have yellow-colored ray florets.

Plants of the new *Osteospermum* differ from plants of the male parent, 'Sunny Florence', primarily in plant habit as plants of the new *Osteospermum* are more outwardly spreading than and not as upright as plants of 'Sunny Florence'.

Plants of the new *Osteospermum* can be compared to plants of *Osteospermum ecklonis* 'Sunny Dark Florence', disclosed in U.S. Plant Pat. No. 18,606. In side-by-side comparisons conducted in Odense, Denmark, plants of the new *Osteospermum* differed from plants of 'Sunny Dark Florence' in the following characteristics:

1. Plants of the new *Osteospermum* were more outwardly spreading than and not as upright as plants of 'Sunny Dark Florence'.
2. Plants of the new *Osteospermum* and 'Sunny Dark Florence' differed in ray floret color as plants of 'Sunny Dark Florence' had dark orange-colored ray florets.

BRIEF DESCRIPTION OF THE PHOTOGRAPHS

The accompanying photographs illustrate the overall appearance of the new *Osteospermum* plant. These photographs shows the colors as true as it is reasonably possible to obtain in colored reproductions of this type. Colors in the photographs may differ slightly from the color values cited in the detailed botanical description which accurately describe the colors of the new *Osteospermum* plant.

The photograph on the first sheet comprises a side perspective view of typical flowering plants of 'Sunbre0901' grown in a container.

The photograph on the second sheet is a close-up view of a typical inflorescence of 'Sunbre0901'.

DETAILED BOTANICAL DESCRIPTION

The aforementioned photographs, following observations and measurements describe plants grown in 25-cm containers in Poeldijk, The Netherlands during the spring in a glass-covered greenhouse and in an outdoor nursery and under conditions and practices which approximate those generally used in commercial *Osteospermum* production. During the production of the plants, day temperatures ranged from 8° C. to 25° C. and night temperatures ranged from 8° C. to 14° C. Plants were pinched one time and were 15 weeks old when the photographs and description were taken. In the following description, color references are made to The Royal Horticultural Society Colour Chart, 2007 Edition, except where general terms of ordinary dictionary significance are used.

Botanical classification: *Osteospermum ecklonis* 'Sunbre0901'.

Parentage:

*Female, or seed, parent.*—Proprietary selection of *Osteospermum ecklonis* identified as code number 90.008.03, not patented.

*Male, or pollen, parent.*—*Osteospermum ecklonis* 'Sunny Florence', disclosed in U.S. Plant Pat. No. 17,307.

Propagation:

*Type.*—Terminal vegetative cuttings.

*Time to initiate roots, summer.*—About twelve days at 18° C.

*Time to initiate roots, winter.*—About 14 days at 18° C. to 20° C.

*Time to produce a rooted cutting, summer.*—About 20 days at 18° C. to 20° C.

*Time to produce a rooted cutting, winter.*—About 28 days at 18° C.

*Root description.*—Medium in thickness, fibrous; light tan in color.

*Rooting habit.*—Freely branching; moderately dense.

Plant description:

*Plant and growth habit.*—Mounding and outwardly spreading plant habit; moderately vigorous growth habit; freely branching habit with about 34 lateral branches developing per plant.

*Plant height.*—About 25.3 cm.

*Plant diameter.*—About 55.3 cm.

*Lateral branch description.*—Length: About 12.5 cm. Diameter: About 4 mm. Internode length: About 1.1 cm. Texture: Smooth, glabrous. Strength: Strong. Color: Close to 144B.

*Foliage description.*—Arrangement/quantity: Alternate, simple; leaves sessile; about eleven leaves per lateral branch. Length: About 5 cm. Width: About 1.1 cm. Shape: Oblanceolate. Apex: Broadly acute. Base: Narrowly cuneate. Margin: Entire with coarse indentations. Texture, upper and lower surfaces: Smooth, glabrous; margins, pubescent. Color: Developing leaves, upper surface: Close to 143A to 143B. Developing leaves, lower surface: Between 143A and 144A. Fully expanded leaves, upper surface: Close to N137B; venation, close to 138B. Fully expanded leaves, lower surface: Close to N137B; venation, close to 138A to 138B.

Inflorescence description:

*Appearance and flowering habit.*—Daisy-type inflorescences; inflorescences face upright and are positioned above and beyond the foliage; inflorescences terminal and axillary; disc and ray florets developing acropetally on a capitulum; freely flowering habit; about 13 inflorescences developing per lateral branch.

*Fragrance.*—Faintly fragrant; musky.

*Flowering response.*—Plants of the new *Osteospermum* begin flowering about ten to twelve weeks after pinching; plants flower continuously from spring to late summer in Northern Europe.

*Inflorescence longevity.*—Inflorescences last about two weeks on the plant; inflorescences not persistent.

*Inflorescence bud.*—Height: About 2.2 cm. Diameter: About 1.4 cm. Shape: Ovoid. Color: Towards the base, between 144C and 145A; towards the apex, between 163A to 163B and N167C.

*Inflorescence size.*—Diameter: About 7.7 cm. Depth (height): About 2.5 cm. Disc diameter: About 1.5 cm. Receptacle diameter: About 4 mm. Receptacle height: About 3 mm.

*Ray florets.*—Length: About 4.4 cm. Width: About 8 mm. Shape: Oblanceolate. Apex: Retuse. Base: Attenuate. Margin: Entire. Texture, upper and lower surfaces: Smooth, glabrous; towards the base, pubescent. Number of ray florets per inflorescence: About 28 arranged in two whorls. Color: When opening, upper surface: Close to N163C to N163D. When opening, lower surface: Close to 166C to 166D; central band, close to 182C. Fully opened, upper surface: Close to 162A. Fully opened, lower surface: Close to 166C to 166D; central band, close to 182C; towards the base, close to 165C.

*Disc florets.*—Shape: Tubular; apex, five-pointed. Length: About 8 mm. Diameter, apex: About 4 mm. Diameter, base: About 1 mm. Number of disc florets per inflorescence: About 90. Color: Immature: Close to 197D; towards the apex, close to N186A. Mature: Towards the apex, close to 174D; mid-section, close to 161D; towards the base, close to 155D flushed with close to 161D.

*Phyllaries.*—Quantity per inflorescence: About 20 arranged in a single whorl. Length: About 1.2 cm. Width: About 1.5 mm. Shape: Lanceolate. Apex: Narrowly acute. Base: Cuneate. Margin: Entire. Texture, upper and lower surfaces: Sparsely pubescent. Color, upper surface: Close to 143A. Color, lower surface: Close to 143A; towards the margins, close to 143C.

*Peduncles.*—Length, terminal peduncle: About 12.4 cm. Length, fourth peduncle: About 19.5 cm. Diameter: About 2 mm. Strength: Strong. Aspect, terminal peduncle: Erect. Aspect, axillary peduncle: About 30° from vertical. Texture: Smooth, glabrous. Color: Close to 144A to 144B.

*Reproductive organs.*—Androecium: Present on disc florets only. Anther shape: Lanceolate. Anther length: About 4 mm. Anther color: Close to N186A. Pollen amount: Abundant. Pollen color: Close to 17B. Gynoecium: Present on both ray and disc florets. Pistil length: About 5 mm. Stigma shape: Tapering. Stigma color: Close to N186A. Style length: About 4 mm. Style color: Close to N186B. Ovary color: Close to 145D.

*Seeds/fruits.*—Seed and fruit development have not been observed on plants of the new *Osteospermum.*

Disease/pest resistance: Plants of the new *Osteospermum* have not been shown to be resistant to pathogens and pests common to *Osteospermums.*

Garden performance: Plants of the new *Osteospermum* have been observed to have good garden performance and be hardy to USDA Zone 9 and to tolerate rain, wind and high temperatures of about 40° C.

It is claimed:

1. A new and distinct *Osteospermum* plant named 'Sunbre0901' as illustrated and described.

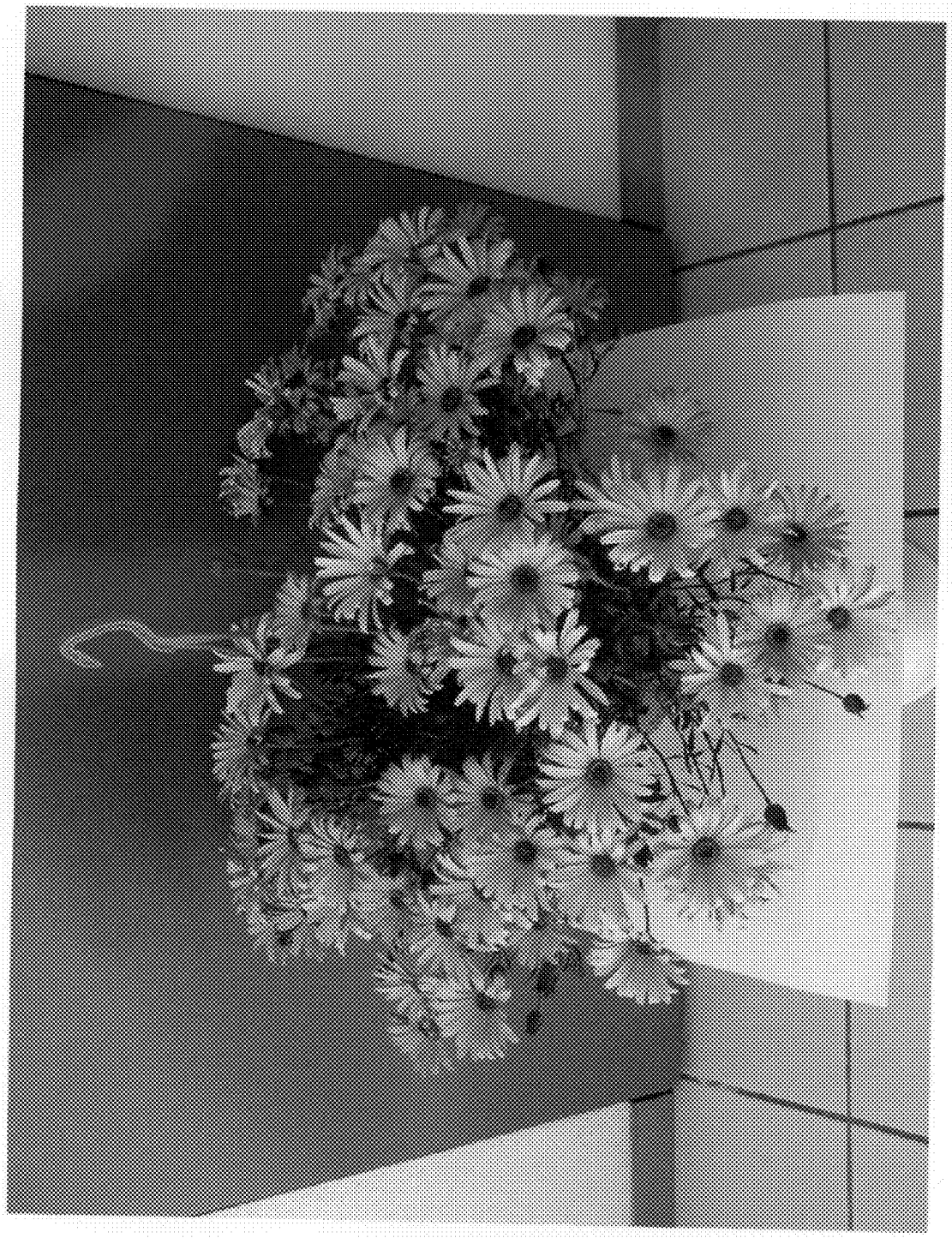

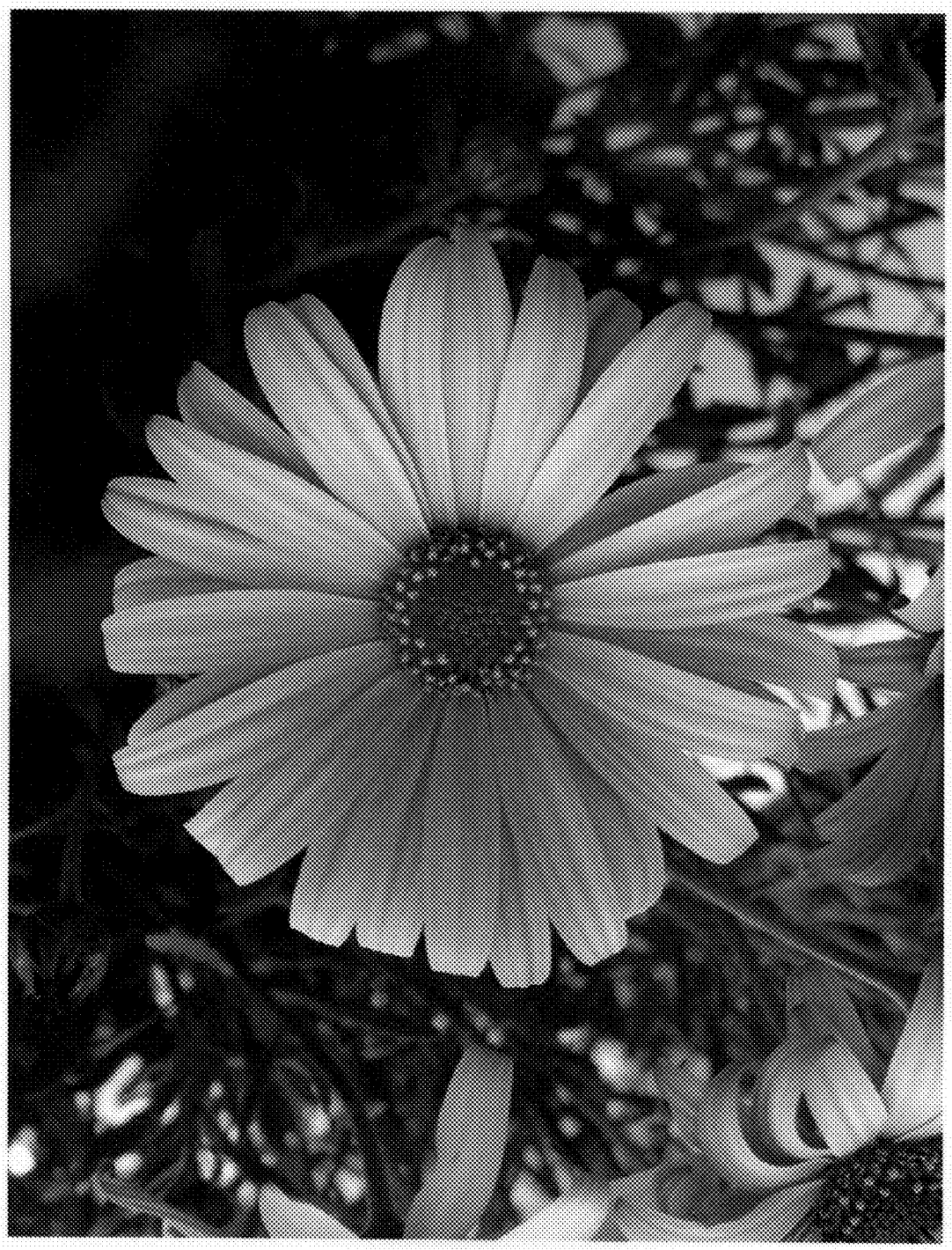

* * * * *